United States Patent [19]

Suzuki

[11] Patent Number: 5,019,349

[45] Date of Patent: May 28, 1991

[54] PIPE FOR MEASURING ERYTHROCYTE SEDIMENTATION RATE

[76] Inventor: Issei Suzuki, 3311-17, Fukami, Yamato-shi, Kanagawa-ken, Japan

[21] Appl. No.: 562,449

[22] Filed: Aug. 1, 1990

Related U.S. Application Data

[63] Continuation of Ser. No. 428,031, Oct. 27, 1989, abandoned, which is a continuation of Ser. No. 925,898, Nov. 3, 1986, abandoned.

[30] Foreign Application Priority Data

Nov. 8, 1985 [JP] Japan ............................ 60-171843[U]

[51] Int. Cl.$^5$ .................. B01L 3/02; G01N 33/49
[52] U.S. Cl. ........................... 422/73; 422/100; 422/101; 436/70; 436/177; 436/180; 73/864.02; 73/864.03
[58] Field of Search ................... 422/61, 100, 101, 73; 73/864.01, 864.02, 864.03; 436/70, 63, 177, 180

[56] References Cited

U.S. PATENT DOCUMENTS

| | | | |
|---|---|---|---|
| 2,692,503 | 10/1954 | Crecelius | 73/864.03 |
| 3,783,696 | 1/1974 | Coleman | 73/864.02 |
| 3,864,979 | 2/1975 | Ayres | 73/864.03 X |
| 3,891,392 | 6/1975 | Betts et al. | 73/864.02 |
| 3,995,496 | 12/1976 | Bickford | 73/864.03 |

FOREIGN PATENT DOCUMENTS 2155566  5/1973  Fed. Rep. of Germany ... 73/864.02

OTHER PUBLICATIONS

Fisher Scientific 1983, Disposable Serological Pipets, pp. 936-937.

*Primary Examiner*—Robert J. Warden
*Assistant Examiner*—Lynn M. Kummert
*Attorney, Agent, or Firm*—Larson and Taylor

[57] ABSTRACT

In a pipe 1 for measuring erythrocyte sedimentation rate, a sealing plug body 3, made of synthetic resin material which passes air but swells when water is absorbed thereby, is inserted into the pipe 1 in such a manner that the lower surface of the plug body 3 may be brought into contact with zero graduation of the pipe 1. The pipe is disposable, and it is possible to measure erythrocyte sedimentation rates easily and at small expense.

2 Claims, 1 Drawing Sheet

PIPE FOR MEASURING ERYTHROCYTE SEDIMENTATION RATE

This application is a continuation of application Ser. No. 07/428,031 filed 27 Oct. 1989, now abandoned, which is a continuation of U.S. Ser. No. 07/925,898, filed Nov. 3, 1986, now abandoned.

BACKGROUND OF THE INVENTION

This invention relates to a pipe for measuring erythrocyte sedimentation rate.

Conventionally erythrocyte sedimentation rate has been measured by using a hollow pipe having about 3 mm inside diameter and about 30 cm length, which is made of glass or synthetic resin and graduated over 20 cm length from its lower portion, by filling said pipe up to zero graduation with blood mixed with an anticoagulant, and by retaining the hollow pipe upright so as to take advantage of the fact that the specific gravity of erythrocyte is heavier than that of blood-plasma. In such a case, the slender, hollow pipe has been filled with blood in such a manner that the blood is sucked in, up to zero graduation, by the mouth or a pump from the upper inlet of the pipe or the blood is charged by a syringe from the lower inlet.

Though such a filling operation seems to be simple it needs skill and experience to prevent said pipe from infection of AIDS, virus hepatitis or venereal diseases such as syphilis, which infection is caused by the blood before or after the use of the measuring pipe of erythrocyte sedimentation rate.

SUMMARY OF THE INVENTION

The present invention provides a pipe for measuring erythrocyte sedimentation rate with certainty by using a simply-constructed pipe but removing the above disadvantages.

An object of the invention is to provide a pipe for measuring erythrocyte sedimentation rate, in which the pipe is graduated, transparent and hollow, and it is inserted with a plug body of air-passing but water-absorbing swellable synthetic resin in such a way that the lower surface of said plug body may correspond with zero graduation.

Said plug body is made of a synthetic resin which freely passes air but has a water-absorbing sealing property in that the resin immediately swells when it has absorbed water. When the lower portion of a pipe for measuring erythrocyte sedimentation rate is inserted into a test tube of blood mixed with an anticoagulant, and the air in the pipe is sucked in with the mouth or pumped out with a pump, the blood in the pipe rises up to reach zero graduation. At this time the plug body absorbs blood and swells immediately, when the pipe is sealed. Erythrocyte sedimentation pipes in such condition are arranged in a row and the columns of red blood corpuscles which are separated from blood-plasma are measured according to graduations at certain regular intervals of time, whereby the erythrocyte sedimentation rates can be measured.

The pipes for measuring erythrocyte sedimentation rate according to the invention can be easily disposed, so that it is possible to eliminate all the troubles such as cleaning, sterilization and drying after using of the pipes, which troubles are seen in known pipes.

DETAILED DESCRIPTION OF THE INVENTION

The invention will now be described more in detail, by way of considering exemplary embodiments, with reference to the accompanying drawings.

Figure 1:
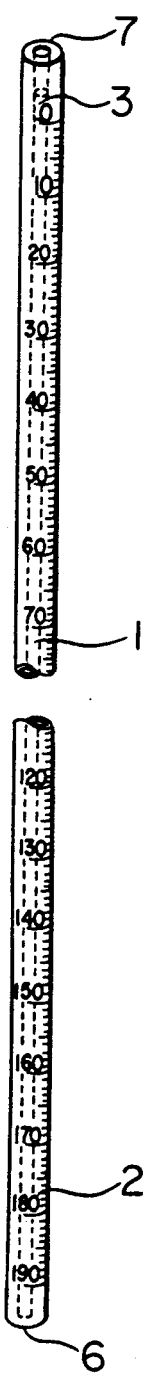
FIG. 1 is a perspective view of a pipe for measuring erythrocyte sedimentation rate according to the present invention.
Figures 2A, 2B:
FIGS. 2a, 2b, 2c and 2d are respectively enlarged explanatory views of four different embodiments of plug bodies.
Figures 2C, 2D:
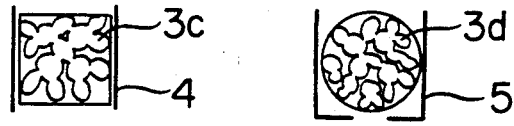

FIG. 1 shows a perspective view of a pipe 1 for measuring erythrocyte sedimentation rate, which is conventionally used. The pipe is slender and it is made either of glass or a synthetic resin. It has about 3 mm inside diameter and usually about 30 cm length and it is provided at its lower portion with graduations 2 in the range 0–20 cm. A plug body 3 is inserted into the pipe in such a manner that the lower surface of the plug body 3 may be brought into contact with zero graduation. FIGS. 2a, 2b, 2c and 2d are enlarged views of modified plug bodies 3 which are used in the pipe of the invention. Said plug bodies can pass air but swell when they absorb water. FIG. 2a shows a cylindrical unit 3a, FIG. 2b a spherical unit 3b, FIG. 2c a cylindrical unit 3c being covered with a cylindrical, synthetic resinous material 4, and FIG. 2d a spherical unit 3d being covered with a cylindrical body 5 having a bottom plate with one opening. As illustrated in FIGS. 2a and 2d, the swellable synthetic resin making up the plug bodies shown in these figures generally comprises interconnected randomly oriented particles or pieces. There is no particular limit on the length having no graduations 2 in the upper portion of the pipe.

Figure 3:
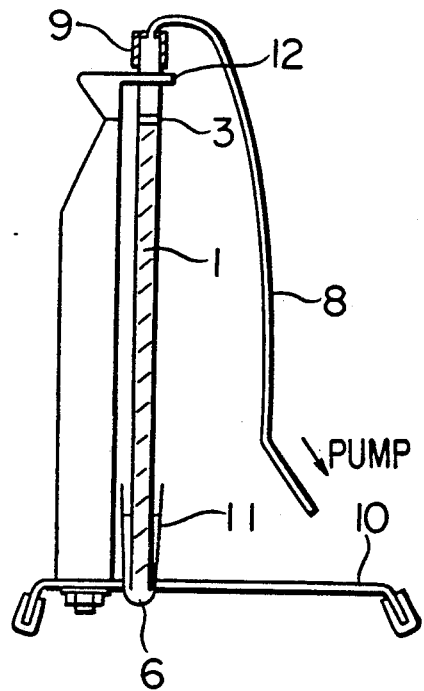
FIG. 3 is a view showing the using state of the pipe according to the invention.

FIG. 3 shows the operation of the present invention, in which a platform 10 is placed with a test pipe 11 accomodating blood mixed with an anticoagulant, the pipe 1 for measuring erythrocyte sedimentation rate is inserted into the pipe 11 through a support frame 12, and a lower inlet 6 of said pipe 1 is positioned within the test pipe 11. When an engaging portion 9 at the end of a flexible suction tube 8 which is connected to a pump covers an upper inlet 7 of the pipe 1 in such condition, the air within the pipe 1 is pumped out through the plug body 3, and when the blood column indicates zero graduation the plug body 3 causes a sealing whereas the blood column becomes stationary at zero graduation. Thereafter by reading the graduation of the blood column after every certain fixed periods of time the erythrocyte sedimentation rate can be measured.

Since the present invention is constituted as described above, it is very easy to measure erythrocyte sedimentation rate and it is easy to manufacture the pipes of the invention thereby presenting economical effects.

What is claimed is:

1. In combination, a graduated, transparent, hollow pipe for measuring erythrocyte sedimentation rates and including a zero level graduation mark, and a spherical plug body of an air-permeable but water-absorbing swellable synthetic resin comprised throughout of interconnected randomly distributed particles and positioned within said hollow pipe such that the lower surface of said plug body is at the same level within the pipe as the zero level graduation mark of the pipe whereby the plug, upon swelling, provides sealing off of the tube to prevent blood from passing beyond the zero level graduation mark.

2. A pipe for measuring erythrocyte sedimentation rate as claimed in claim 1 wherein the plug body is received within a cylindrical body of a synthetic resin and having a bottom plate with an opening therein.

* * * * *